US 6,737,419 B2

(12) United States Patent
Sherman

(10) Patent No.: US 6,737,419 B2
(45) Date of Patent: May 18, 2004

(54) BENAZEPRIL HYDROCHLORIDE TABLET FORMULATIONS

(76) Inventor: Bernard Charles Sherman, 50 Old Colony Road, Ontario (CA), M2L 2K1

( * ) Notice: Subject to any disclaimer, the term of this patent is extended or adjusted under 35 U.S.C. 154(b) by 175 days.

(21) Appl. No.: 10/120,388

(22) Filed: Apr. 12, 2002

(65) Prior Publication Data

US 2002/0183308 A1 Dec. 5, 2002

(30) Foreign Application Priority Data

Apr. 12, 2001 (CA) ............................................. 2343949

(51) Int. Cl.⁷ ............................................... A61K 31/55

(52) U.S. Cl. .............. 514/212.07; 514/494; 514/212.07; 514/213; 514/215; 514/217

(58) Field of Search ............................ 514/494, 212.07, 514/213, 215, 217, 354

(56) References Cited

U.S. PATENT DOCUMENTS

| 4,410,520 | A | | 10/1983 | Watthey | |
|---|---|---|---|---|---|
| 6,372,255 | B1 | * | 4/2002 | Saslawski et al. | .......... 424/473 |
| 6,652,882 | B1 | * | 11/2003 | Odidi et al. | ................ 424/486 |

* cited by examiner

Primary Examiner—Sabiha Qazi
(74) Attorney, Agent, or Firm—Nixon & Vanderhye PC

(57) ABSTRACT

Stable tablets comprising benazepril hydrochloride are prepared by employing zinc stearate as the lubricant.

4 Claims, No Drawings

BENAZEPRIL HYDROCHLORIDE TABLET FORMULATIONS

BACKGROUND OF THE INVENTION

Benazepril hydrochloride is a medicinal compound useful as an antihypertensive agent. Its ability to inhibit the angiotension converting enzyme and thus lower blood pressure is disclosed in U.S. Pat. No. 4,410,520.

Tablets comprising benazepril hydrochloride are sold in the United States and elsewhere under the tradename Lotensin™. These tablets comprise, in addition to benazepril hydrochloride as active ingredient, various inactive ingredients, which include a lubricant to avoid sticking to the punches in the tabletting process.

According to the literature for Lotensin™, the lubricant used in the 5 mg and 10 mg tablets is hydrogenated castor oil, while that used in the 40 mg tablets is magnesium stearate. Magnesium stearate is the most commonly used lubricant in pharmaceutical tablets. However, it accelerates the rate of degradation of benazepril hydrochloride, so that benazepril hydrochloride tablets which comprise magnesium stearate have a shorter shelf life than would be the case without magnesium stearate.

It appears that Lotensin™ 5 mg and 10 mg tablets are made using hydrogenated castor oil instead of magnesium stearate as a lubricant in order to achieve a lower degradation rate. It further appears that 40 mg tablets could not be made using hydrogenated castor oil as the only lubricant (i.e. without magnesium stearate) because hydrogenated castor oil is relatively ineffective as a lubricant, and is not sufficiently effective to eliminate sticking in the higher strength (40 mg) tablets.

The 40 mg strength of Lotensin™ tablets thus has a relatively high degradation rate.

The object of the present invention is thus to provide a lubricant for benazepril hydrochloride tablets that is more effective than hydrogenated castor oil as a lubricant, but does not cause degradation of the benazepril hydrochloride to the same extent as does magnesium stearate.

SUMMARY OF THE INVENTION

It has been found that zinc stearate is an effective lubricant for benazepril hydrochloride tablets.

Moreover, it has been surprisingly found that the rate of degradation of benazepril hydrochloride in tablets comprising zinc stearate as lubricant is much lower than in tablets comprising magnesium stearate as lubricant.

The invention is thus a pharmaceutical tablet comprising benazepril hydrochloride and zinc stearate as the lubricant.

DETAILED DESCRIPTION OF THE INVENTION

In addition to benazepril hydrochloride as the active ingredient, and zinc stearate as the lubricant, the tablet formulation will also comprise at least one other excipient as a filler and binder, such as, for example, microcrystalline cellulose or lactose. The preferred filler is microcrystalline cellulose.

The tablet will also optionally comprise a disintegrant, such as, for example, starch, croscarmellose sodium, sodium starch glycolate, or crospovidone. The preferred disintegrant is crospovidone. The tablet will also optionally comprise other excipients, such as colloidal silicon dioxide as glidant, or a colour agent. The tablets will also optionally contain another active ingredient, such as a diuretic.

The quantity of the lubricant as a percentage of the total tablet weight will preferably be from about 0.2 percent to about 3.0 percent.

The benazepril hydrochloride tablets of this invention can be prepared by conventional tablet forming techniques such as, for example, wet granulation and dry granulation. In the wet granulation process, the active ingredient or ingredients are mixed with some or all of the filler. This blend is then wet granulated with a solution of a binder in solvent. The resultant wet mass is then dried and milled. The granules are then mixed with the remaining ingredients, which will include the lubricant, to produce the final mix, which is then compressed into tablets.

In the dry granulation process, the active ingredient or ingredients are mixed with the other ingredients without addition of any solvent, and thus without the need for drying. Again the final mix is compressed into tablets. The dry granulation approach is preferred, as it is simpler and thus less costly.

The invention will be further understood from the following examples:

| Example No: | 1 | 2 |
|---|---|---|
| Benazepril Hydrochloride | 40.0 | 40.0 |
| Microcrystalline Cellulose | 58.7 | 57.2 |
| Crospovidone | 0.5 | 2.0 |
| Colloidal Silicon Dioxide | 0.2 | 0.2 |
| Magnesium Stearate | 0.6 | X |
| Zinc Stearate | X | 0.6 |
| | 100.0 | 100.0 |

For each of the 2 examples, the ingredients in the proportions listed were mixed together. The powder mixture was then passed through a #60 screen and mixed again. The powder mixture was then compressed into tablets of weight 100 mg each, so that each tablet contained 40 mg of benazepril hydrochloride.

Tablets of each of the examples as well as Lotensin™ tablets 40 mg were stored at 60° C. for two weeks and then tested by an HPLC method to determine the degradation products as a percentage of the initial benazepril hydrochloride content.

The results were as follows:

| Example No. | Lubricant | % Degradation Products |
|---|---|---|
| 1 | Magnesium Stearate | 1.24% |
| 2 | Zinc Stearate | 0.57% |
| Lotensin ™ 40 mg | Magnesium Stearate | 1.68% |

It can be seen that the percentage degradation is much lower for th tablets of example 2 (which comprise zinc stearate as lubricant) than for either the tablets of example 1 or Lotensin™ 40 mg tablets, both of which comprise magnesium stearate.

It is thus found that, while degradation rate is relatively high when magnesium stearate is used as lubricant, the degradation rate is much lower when zinc stearate is used as lubricant.

What is claimed is:

1. A pharmaceutical tablet comprising benazepril hydrochloride and zinc stearate.

2. A tablet as in claim 1 further comprising microcrystalline cellulose.

3. A tablet as in claim 2 further comprising crospovidone.

4. A tablet as in claim 1 where the amount of lubricant by weight is from about 0.2 percent to about 3 percent of the total tablet weight.